(12) United States Patent
Shemmann

(10) Patent No.: US 11,504,464 B2
(45) Date of Patent: Nov. 22, 2022

(54) BLOOD CENTRIFUGE WITH SEPARATION, SENSOR AND DISPENSE CONTROL SYSTEM

(75) Inventor: Marcel F Shemmann, Maria Hoop (NL)

(73) Assignee: FOCE Technology International BV, Maria Hoop (NL)

( * ) Notice: Subject to any disclaimer, the term of this patent is extended or adjusted under 35 U.S.C. 154(b) by 2209 days.

(21) Appl. No.: 13/816,260

(22) PCT Filed: Aug. 9, 2011

(86) PCT No.: PCT/US2011/001407
§ 371 (c)(1),
(2), (4) Date: Jan. 21, 2016

(87) PCT Pub. No.: WO2012/021167
PCT Pub. Date: Feb. 16, 2012

(65) Prior Publication Data
US 2021/0322663 A1    Oct. 21, 2021

Related U.S. Application Data

(60) Provisional application No. 61/371,808, filed on Aug. 9, 2010.

(51) Int. Cl.
| | |
|---|---|
| *B04B 5/04* | (2006.01) |
| *B04B 9/14* | (2006.01) |
| *B04B 13/00* | (2006.01) |
| *A61M 1/36* | (2006.01) |

(52) U.S. Cl.
CPC ........ *A61M 1/3698* (2014.02); *A61M 1/3696* (2014.02); *B04B 5/0442* (2013.01); *B04B 9/14* (2013.01); *B04B 13/00* (2013.01); *A61M 2205/3306* (2013.01); *B04B 2009/143* (2013.01); *B04B 2013/006* (2013.01)

(58) Field of Classification Search
CPC .............. A61M 1/3698; A61M 1/3696; A61M 2205/3306; B04B 9/14; B04B 13/00; B04B 5/0442; B04B 2009/143; B04B 2013/006
USPC ..................................... 494/41, 45
See application file for complete search history.

(56) References Cited

U.S. PATENT DOCUMENTS

| | | | | |
|---|---|---|---|---|
| 4,790,807 A | * | 12/1988 | Neumann ............. | B04B 5/0428 494/45 |
| 5,603,845 A | * | 2/1997 | Holm ........................ | B04B 7/00 210/782 |
| 5,723,050 A | * | 3/1998 | Unger ................... | B04B 5/0428 210/360.1 |

(Continued)

*Primary Examiner* — Charles Cooley
(74) *Attorney, Agent, or Firm* — Rowan TELS LLC

(57) ABSTRACT

A centrifuge is configured to provide integrated separation of blood components such that the separated products remain spinning within the centrifuge during the separation process. The centrifuge includes a disposable configured to separate the blood components such that the separated products remain within the disposable while the centrifuge is spinning; an integrated sensor system capable of determining a composition of the separated products within the disposable while the centrifuge is spinning; a chamber having a non-circular section that is configured to be deliberately un-balanced when the centrifuge chamber is empty; and the disposable includes valves that rotate with the centrifuge chamber.

10 Claims, 18 Drawing Sheets

(56) References Cited

U.S. PATENT DOCUMENTS

Figure 1:
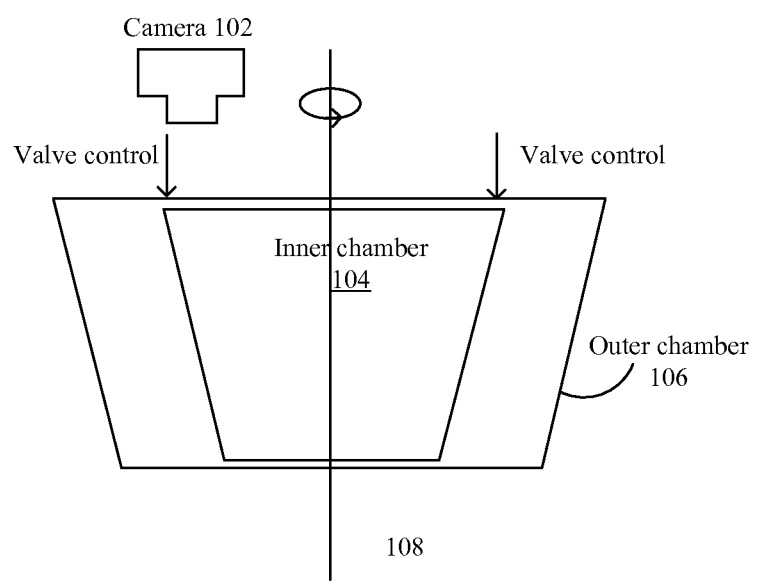

| | | | | |
|---|---|---|---|---|
| 7,413,665 B2 * | 8/2008 | Holmes | ............... | A61M 1/3641 |
| | | | | 210/257.1 |
| 8,287,742 B2 * | 10/2012 | Holmes | ............... | A61M 1/3695 |
| | | | | 210/782 |
| 8,337,380 B2 * | 12/2012 | Ellingboe | ............... | B04B 15/06 |
| | | | | 494/45 |
| 8,425,448 B2 * | 4/2013 | Felt | ............... | A61M 1/3672 |
| | | | | 604/6.04 |
| 2008/0220959 A1 * | 9/2008 | Holmes | ................ | B04B 5/0428 |
| | | | | 494/45 |
| 2011/0224062 A1 * | 9/2011 | Pobitschka | ......... | A61M 1/0272 |
| | | | | 494/5 |
| 2021/0322663 A1 * | 10/2021 | Schemmann | ........... | B04B 13/00 |

* cited by examiner

BLOOD CENTRIFUGE WITH SEPARATION, SENSOR AND DISPENSE CONTROL SYSTEM

PRIORITY

This application claims priority under 35 U.S.C. 372 as a USA national stage application of PCT application no. PCT/US2011/001407, filed on 9 Aug. 2011, which claims priority to U.S. provisional application No. 61/371,808 filed on 9 Aug. 2010.

TECHNICAL FIELD

The present disclosure relates to, but is not limited to, material separation devices and techniques.

BACKGROUND ART

A centrifuge is a piece of equipment, generally driven by an electric motor (some older models were spun by hand), that puts an object in rotation around a fixed axis, applying a force perpendicular to the axis. The centrifuge works using the sedimentation principle, where the centripetal acceleration causes more dense substances to separate out along the radial direction (the bottom of the tube). By the same token, lighter objects will tend to move to the top.

There are various known designs for centrifuges, including preparative centrifuges, analytical centrifuges, angle fixed centrifuges, swing head centrifuges, haematocrit centrifuges, and continuous tubular centrifuges. Screen centrifuges allow a liquid to pass through a screen of some sort, through which the solids cannot go (due to granulometry larger than the screen gap or due to agglomeration). Common types of screen centrifuges are pusher centrifuges, peeler centrifuges, decanter centrifuges (in which there is no physical separation between the solid and liquid phase, rather an accelerated settling due to centrifugal acceleration), and continuous liquid centrifuges.

SUMMARY OF THE INVENTION

Technical Problem

Conventional centrifuges for blood separation may not produce adequate component separation and controllability of the result for certain modern applications. Conventional centrifuges are often inadequate for producing needed quality/quantity of certain products, such as platelet rich plasma (PRP) is used in various applications such as wound treatment or enhancement of recovery after operations.

Conventional centrifuges, especially those designed to rest on a laboratory table top, may not adequately detect the demarcation between different blood components (which in some cases is gradual) or have the capability to select a certain range of the product.

Solution to the Problem

A novel centrifuge includes integrated separation of blood components so that the separated products remain spinning within the centrifuge during the separation process. The separation process may be monitored by a sensor, such as a camera or optical sensor. The centrifuge or an associated device (such as a computer) may include logic to determine the composition of the product produced by the centrifuge, while the centrifuge is running. The sensor system may include a particle counter capable of counting blood platelets and/or different types of blood cells. The sensor system may be capable of determining the hematocrit value of the blood. A dilution stage may be used to prepare the product measurement for the actual sensor. The dilution stage may include a weight measurement of the product, and the centrifuge may produce a sample for the sensor system. The weight measurement may be derived from a balance measurement of a spinning centrifuge. The measurement may include an optical measurement of collected and diluted volumes.

The sample may be taken throughout the duration of the product production, such that the sample is representative for the entire volume of product collected. The sample may be moved from a sterile part of the centrifuge to a non sterile part containing the composition sensor system.

The result of the composition measurement may be used to adjust the product composition, and the composition adjustment integrated in the centrifuge, for example in the disposable. The composition adjustment may be performed by re-spinning the centrifuge. The centrifuge can include a mechanism for taking a volumetric measurement of product and for diluted product.

A blood centrifuge process includes blood component separation, sample collection, product composition measurement and product dilution to a desired composition. The product may remain on a centrifuge within a disposable during the entire process. All fluid containing sterile parts of the disposable rotate with the centrifuge chamber when it is spinning. A database of target product compositions may be used along with a user interface to enter target product compositions or treatment methods. A measurement may be made of at least one blood composition component before the centrifuge process begins. An expected product volume per unit blood may be loaded into the centrifuge to provide the user with an instruction on the amount of blood to enter into the centrifuge to make the product.

The separation of components may be controlled by the type of end product required, for example using a sensor such as a camera to select the components required from the centrifuge. The sensor output may be provided to the user who can adjust the components being separated in the centrifuge process. The system may compare a determined product composition to a target and may compute a dilution required to obtain the desired product composition.

The system may determine a product volume and may dilute the product to the target specification based on a determined amount of dilution needed. A database of past runs can be evaluated to obtain better predictability of the product that can be obtained and where this past information can be used by the arithmetic unit to improve predictions.

The centrifuge can have a non circular section for the centrifuge chamber, and may be deliberately un-balanced in a controlled fashion. Exemplary potential shapes for the centrifuge chamber are elliptical and egg shaped. The centrifuge can include integrated valves that can be actuated during the centrifuge process. Multiple valves can be actuated to produce one or more separation components of the centrifuge process. The valves can be used to balance the centrifuge. The centrifuge can include a mechanism to measure the un-balance of the centrifuge.

A non-circular part of the centrifuge chamber may be formed to be thinner than the rest of the chamber. The aforementioned valves may be located at the thin part of the chamber. Controllable counter weights may be used to adjust the balance of the centrifuge. The valves may be located in the lower part of the centrifuge.

A disposable for a blood centrifuge can include valves that rotate with the centrifuge chamber. The centrifuge system can have a non-circular chamber section with integrated optical sensor system where the optical sampling by the sensor is synchronized with the chamber rotation. Stroboscopic lighting can be synchronized with the chamber to synchronize the sampling. The stroboscopic lighting can be sequenced with different colors to obtain sensor information at different colors. The centrifuge can have at least two main chambers that are approximately balanced, an inner chamber that contains the un-separated start product and at least one intermediate or outer chamber that collects a significant volume of a separation product. The centrifuge can include a syringe spinning with the main chamber that can be filled with the desired fluid component. A sample volume of the component filled into the syringe can be tapped. The sample component can be filled into a second syringe (typically thinner). The second syringe motion can be coupled with the first syringe. The pressure due to the centrifugal force can be used to press the product into the syringe. The centrifuge can be designed to capture leaked fluid after removal of the sample or sample container either by avoiding any leaking or by capturing leaks by gravity and centrifugal force. The composition measurement system need not be sterile and may be provided with a sample in a sample container taken out of the sterile centrifuge section of the system.

Advantageous Effects of the Invention

Performing blood separation within a running centrifuge may result in benefits over prior approaches. For example, better separation and controllability of the result may occur. A simpler disposable design that does not employ rotating seals is disclosed. The design may be employed for instance in small table top centrifuges that are used for immediate treatment of patients after a desired product has been created from blood taken from a patient. For instance, platelet rich plasma (PRP) is used in various applications such as wound treatment or enhancement of recovery after operations.

The disclosed embodiments may prove useful to monitor the demarcation between different blood components (which in some cases is gradual) and to select a certain range of the product. Visual inspection of the blood in the centrifuge may provide sufficient information to detect the relevant demarcations such that a color camera may be employed for this function. The camera may be supported or replaced by IR measurements and other techniques, for instance laser based detection methods.

DESCRIPTION OF EMBODIMENTS

Preliminaries

References to "one embodiment" or "an embodiment" do not necessarily refer to the same embodiment, although they may.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list.

"Logic" refers to machine memory circuits, machine readable media, and/or circuitry which by way of its material and/or material-energy configuration comprises control and/or procedural signals, and/or settings and values, that may be applied to influence the operation of a device. Magnetic media, electronic circuits, electrical and optical memory (both volatile and nonvolatile), and firmware are examples of logic. Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

Those skilled in the art will appreciate that logic may be distributed throughout one or more devices, and/or may be comprised of combinations of instructions in memory, processing capability, circuits, and so on. Therefore, in the interest of clarity and correctness logic may not always be distinctly illustrated in drawings of devices and systems, although it is inherently present therein.

The techniques and procedures described herein may be implemented via logic distributed in a centrifuge and/or one or more associated devices. The particular distribution and choice of logic is a design decision that will vary according to implementation.

Overview

Devices and techniques disclosed herein for blood component separation may also be applied to other fields such as fat component separation and stem cell separation. The techniques involve a centrifuge with integrated separation of blood components such that the separated products remain spinning within the centrifuge during the separation process. A disposable element is included for a blood centrifuge that performs the task of separation of blood components, such that the separated products remain within the spinning disposable during the separation process. The separation is performed while the centrifuge is running, and the separation process may be monitored by a sensor, such as an optical sensor or a camera.

Once the blood has been separated a required concentration of blood platelets is needed for a subsequent treatment process. The sensor supported separation process in the centrifuge provides enhanced control over the separated product. However, the actual platelet concentration and activity thereof varies from patient to patient. The uncertainty may be greater than can be permitted for a treatment process. An enhanced blood centrifuge may include a sensor system able to determine the composition of the product. One method to do this is to pass a diluted sample of the product through a platelet counter, usually a large piece of equipment at a separate location from the blood centrifuge. This makes it impossible to apply the product from a blood centrifuge immediately after it has been obtained at a treatment facility. A sensor system may be included on the blood centrifuge that is able to provide the required measurement accuracy for instance on platelet count.

The platelet count (or other blood component) sensor may be integrated in the disposable. However, such a sensor can be costly and therefore may reside in the centrifuge but outside the disposable. After blood component separation a sample can be provided to the sensor which determines the composition. After this is done the required dilution of the separated product is known to arrive at the correct composition of the product. Preferably this dilution process is performed in the same centrifuge, and preferably within the same disposable. This can be accomplished for instance by re-spinning the centrifuge again and permitting a desired amount of dilution (usually by blood plasma) into the product container within the disposable. Preferably the disposable includes means to take a representative product sample without risk of product contamination, measure the amount of product collected and control the amount of dilution required after the product composition has been measured.

Thus, a blood centrifuge may comprise an integrated sensor system capable of determining the composition of the product produced by the centrifuge. The sensor system may include a particle counter, may be capable of counting blood platelets, may be capable of counting different types of blood cells, and/or may capable of determining the hematocrit value of the blood. The sensor system may include a dilution stage to prepare the product measurement for the actual sensor. The dilution stage may include a weight measurement of the product. The centrifuge may produce a sample for the sensor system, and the sample may be taken throughout the duration of the product such that the sample is representative for the entire volume of product collected. The sample may be moved from a sterile part of the centrifuge to a non sterile part containing the composition sensor system. The result of the composition measurement may be used to adjust the product composition, and the composition adjustment may be integrated in the centrifuge, integrated in the disposable element, and/or performed by re-spinning the centrifuge.

The centrifuge may include a means for a volumetric measurement of product and for diluted product. The measurement may be based on a weight measurement, such as one derived from a balance measurement of a spinning centrifuge. The measurement may include an optical measurement of collected and diluted volumes. The centrifuge may perform blood component separation, sample collection, product composition measurement and product dilution to a desired composition, all using a single piece of equipment in which the product remains on a centrifuge within a disposable during the entire process. All fluid containing sterile parts of the disposable rotate with the centrifuge chamber when it is spinning.

Preferably the centrifuge produces a target product composition. The target composition varies widely depending on the application of the product. For instance, it may be used in an operation, for wound treatment or for other applications. Depending on the patient the target composition may also vary. For this reason the centrifuge system will preferably include a means to determine specifics of the patient blood composition. This may include a measurement before the component separation in the centrifuge, a so-called "whole blood" measurement. This measurement can affect both the desired output composition of the centrifuge and dilution process and the amount of product that can be expected given a volume of blood taken from the patient. The centrifuge preferably includes a database of product composition and volume required for different treatments. The user enters the desired treatment process or target composition and/or volume. The centrifuge system then works towards providing that product. First, it may use a whole blood measurement to provide a refined target (for such cases where the product requirement depends on whole blood composition) and to determine the amount of blood that needs to be taken from the patient to produce the product. If this measurement is not available then it may use a typical estimate for the amount of blood that will be required. Second, it may adjust the product selection during the centrifuge process to the treatment needs. Some treatments may allow a larger fraction of red blood cells in the product than other treatments. In case a larger fraction of red cells is allowed the product volume (for instance PRP) can be increased. The presence of white blood cells may also be of importance further affecting the duration of the centrifuge process and the selection of the product. Once the product has been produced and sampled, the sample measurement may be compared to the target value from the database, user inputs, or computed, and the whole blood measurement result. The centrifuge system may then compute the required dilution of the product and perform the dilution. The end product thus meets the requirement for the intended treatment.

A centrifuge system may thus comprise a database of target product compositions. The centrifuge may comprise a user interface to enter target product compositions or treatment methods, and may provide a measurement of at least one blood composition component before the centrifuge process begins. The centrifuge may comprise an arithmetic unit that computes the expected product volume per unit blood loaded into the centrifuge and provides the user with an instruction on the amount of blood to enter into the centrifuge to make the product. The separation of components may be controlled by the type of end product required.

The output of a sensor may be used to control the centrifuge process of separation of components, and a camera may be employed to select the components required from the centrifuge. The sensor output may be provided to the user and the user has a user interface to adjust the components being separated in the centrifuge process. The centrifuge system may include a measurement of product composition and may include an arithmetic unit that compares product composition to a target and computes a dilution required to obtain the desired product composition, including a determination of product volume. The centrifuge may include a means to dilute the product to the target specification where the amount of dilution is computed by an arithmetic unit. The centrifuge system may include a database of past runs that can be evaluated to obtain better predictability of the product that can be obtained where this past information may be used by the arithmetic unit to improve predictions. The centrifuge may be applied to bodily fluids or fluid components such as fat, red blood cells, white blood cells, or stem cells. A user interface may be integrated in the centrifuge system or (parts of) the interface may be implemented on a computer system that is connected to the centrifuge via a wired or a wireless interface.

Example 1

FIG. 1 illustrates an embodiment of a centrifuge comprising a normal centrifuge chamber and additional chambers external or internal to the normal chamber. One or more mechanisms are used to permit or block flow to these additional chambers. The mechanisms may be based on (electro-) mechanical, magnetic or pneumatic actuation. The control of these mechanisms may involve a window into the running centrifuge that is sufficiently transparent to permit visual remote and contact-less monitoring of the separation process. This permits the monitoring means to be non-disposable. However a disposable camera may be cost effective.

The exemplary centrifuge has an inner 104 and an outer chamber 106. When the blood is spun around an axis 108 the heavier red cells migrate to the outer wall of the inner chamber 104. A valve control mechanism permits blood to exit the inner chamber 104 into the outer chamber 106 that takes on the red cells. Valve control is supported with a camera 102 that observes the demarcation between red cells and other blood components. The outer chamber 106 may be shaped such that blood permitted into the second chamber 106 is not splattered against the outer wall.

Examples 2 and 3

Figure 2:
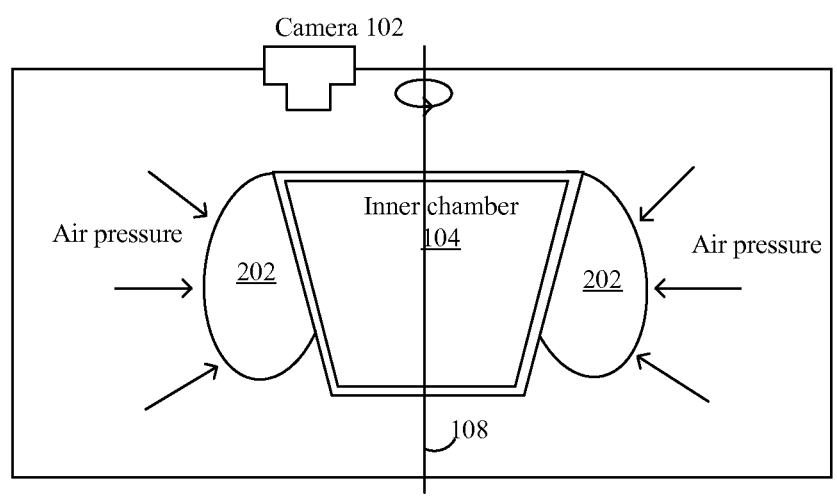

FIG. 2 illustrates an embodiment in which control of the flow into the extra chamber(s) is facilitated by air pressure. The second chamber 202 may be flexible, with pressure applied to the outside of the second chamber 202 to keep fluid out of that chamber. By regulating the pressure the blood (or other material) may be separated into at least two components. This approach involves a pressure relief for the inner chamber 104.

Figure 3:
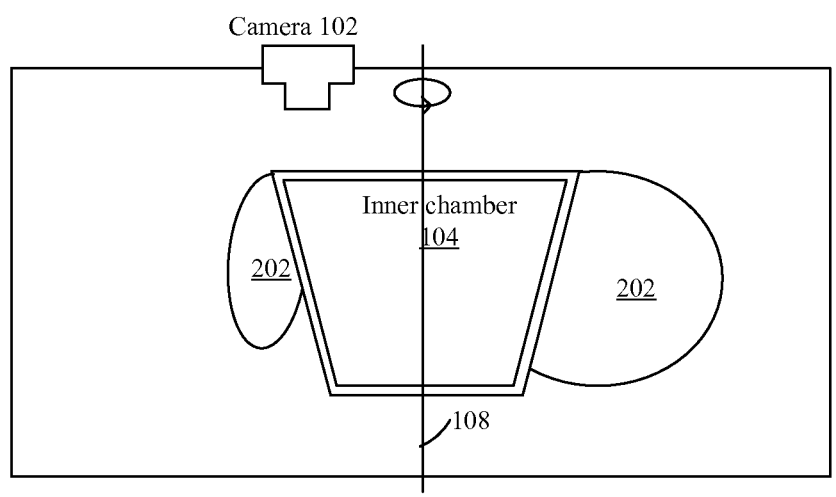

FIG. 3 illustrates what can happen when the flexible outer chamber 202 bulges on one side and destabilize the centrifuge. For small volumes (such as PRP collection) the air pressure concept with a flexible bag remains interesting but for large volume it may be problematic.

Example 4

Figure 4:
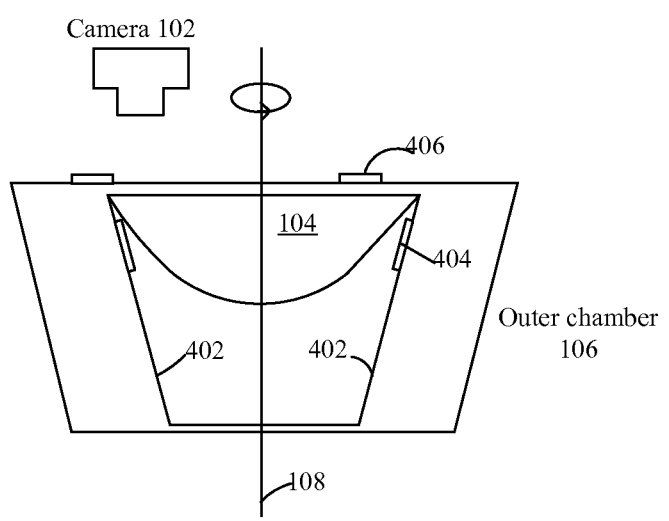

FIG. 4 illustrates an embodiment employing gravity-assisted control of separation. The fluid in the centrifuge climbs up the sidewalls 402 which widen towards the top of the centrifuge. The height to which the fluid climbs depends on the RPM of the centrifuge. If the inner chamber 104 has a spillover 404 at the top into the second chamber 106 (both constructed for example of a hard plastic material) the RPM of the centrifuge may be used to determine the volume transferred into the second chamber 106.

The chamber dimensions to obtain a practical device depend on the centrifuge process. The inclination angle of the sidewalls 402 may result in a design that is too long to be practical. Anywhere along the upper ring of the centrifuge one or more valves 406 may be installed. These can be operated for instance with an external magnetic field acting on a ring of magnetic material. Having a magnetic field that emanates outside the centrifuge may not be desirable. Another option is to have pressure points that can be actuated via the lid on the centrifuge. These actuators rotate with the centrifuge, which is possible with mechanical design, pneumatic design and (brushless) electrical design.

Example 5

Figure 5:
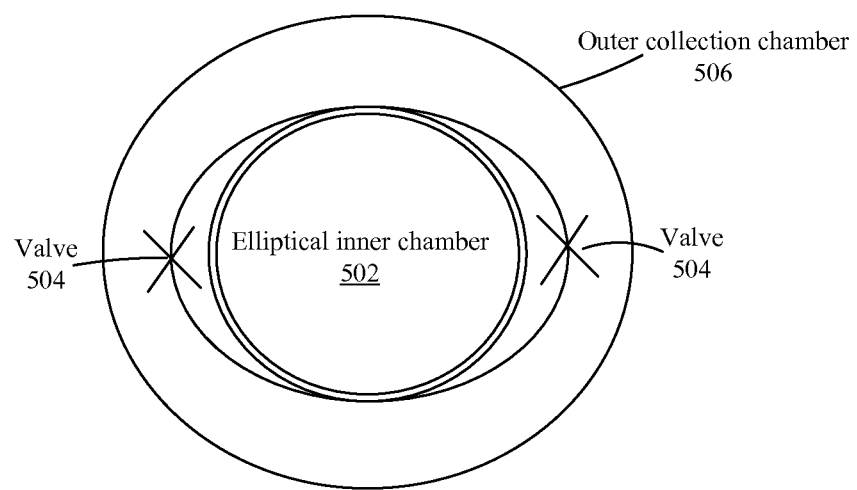

FIG. 5 illustrates an elliptically shaped centrifuge. Certain valve designs may separate into more than two components. For three or more components the centrifuge may be modified into an elliptical shape. For a balanced centrifuge this brings the heaviest fluid components to the ends of the long axis of the ellipse. At those ends valves may be located. With a slightly flexible centrifuge external force or pressure deforms the ellipse such that the orientation of the long axis is changed. This allows directing of the heavy components in the fluid towards different valves. These valves may be selected in the centrifuge process. Alternately, a controllable un-balancing of the centrifuge on either end of an ellipse, or any point upon a circle, may be selected for the heavy components. Thus two or more valves for different fluid component output may be selected.

In FIG. 5, the elliptical inner chamber 502 spins. The fluid components form circles around the axis of rotation and the heaviest components concentrate at the long axis ends of the ellipse. Only two valves 504 are needed that can be located at the ellipse ends. The outer collection chamber 506 can hold the separated fluid or be allowed to drain into a collection vessel or bag. If the drain is based on gravity then a complex seal may not be required.

In one embodiment a centrifuge comprises a non circular section of the centrifuge chamber. The centrifuge may be deliberately un-balanced, and the un-balance may be controlled. A centrifuge may comprise integrated valves that may be actuated during the centrifuge process. The centrifuge may comprise an elliptic shaped section of the chamber, for example an egg shaped section of the chamber. (FIG. 5)

Example 6

Figure 6:
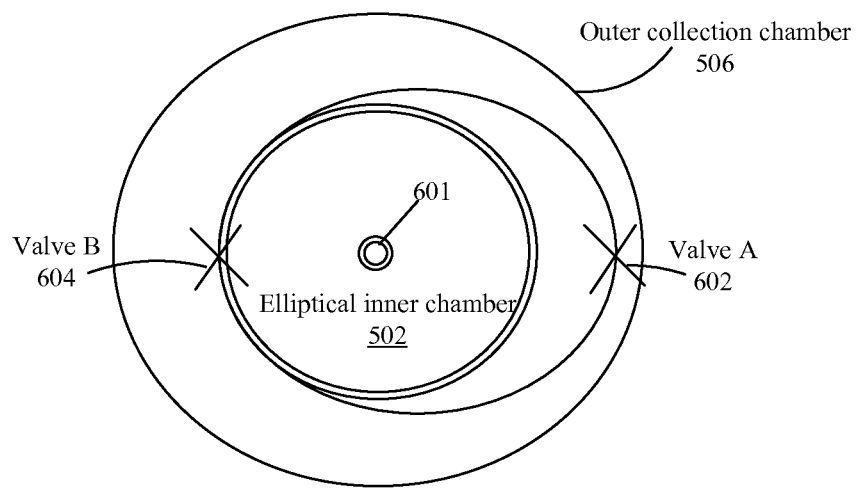

FIG. 6 illustrates a centrifuge with the axis of rotation 601 deliberately off-center. The heavy components can be made to concentrate on one end of the ellipse 603. The axis of rotation 601 is represented with the small central circle. Valve A 602 will collect red blood cells. After these are collected the axis of rotation may be shifted (mechanically or with electromechanical actuators) to select valve B 604 to collect PRP. For different shapes more outputs may be created. The mechanism to control the axis of rotation 601 may be built into the non-disposable part of the centrifuge.

Example 7

Figure 7:
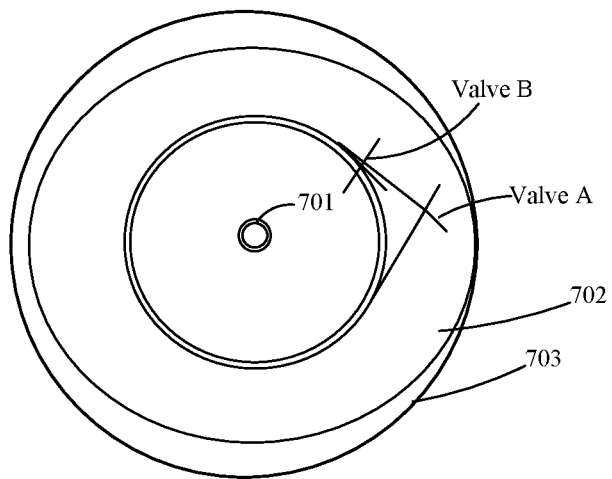

FIG. 7 illustrates a centrifuge with an egg shaped chamber 702. This enables the chamber 702 to be balanced while moving the heavy component to one side. The drawing is exaggerated. The two main output valves A&B are located close to each other, where valve A controls the output of red cells to a circular chamber 703 and valve B is set slightly closer to the axis 701 to select the next lighter component. The interface of that component (the PRP) can be adjusted in front of valve B by adjusting the out-flow on valve A. Then valve B can drain the desired fraction. This arrangement has multiple advantages. The out-flow on valve B can be started at a controllable moment, settable by valve A during the time that the fraction is visible at valve B and being adjusted there. The spinning mass can be kept centered around the axis 701, a de-center is not required during the process. The fluid is not displaced in the centrifuge when transferring from one stage of separation (valve A) to the next stage.

Examples 8 and 9

Figure 8:
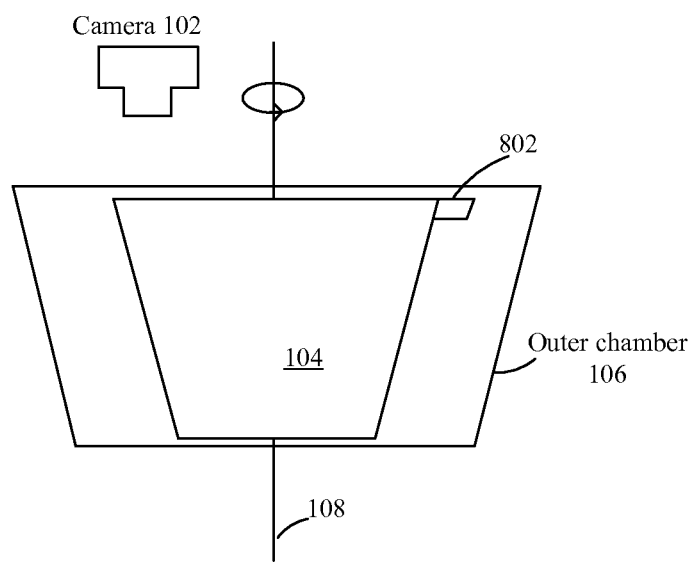
Figure 9:
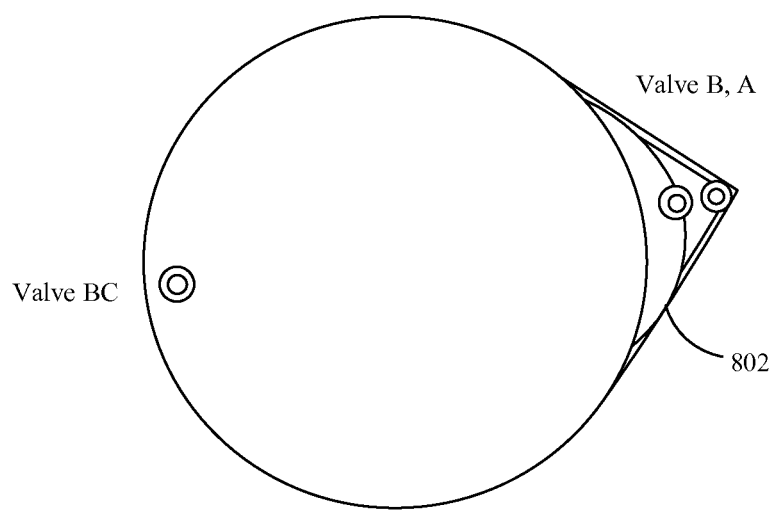

FIGS. 8 and 9 illustrate a centrifuge having a beaker shaped extension 802 towards the valves. The extension is thin and has a low volume, which forces the transition area between the fluids to spread out over a large area. This eases manufacture of valves and spreads out the transition in front of the camera 102. Preferably the section is shaped such that it just slightly larger than needed to hold the amount of PRP that is expected. That permits collection of all the PRP in this section and a clear definition of the transitions in front of the camera 102 before PRP extraction at valve B starts. The valves may then be simple "needle" valves as shown in FIG. 9, where the size of the holes can be fairly large if the thickness of the area with the valves is kept low enough.

A valve BC is shown (Balance Control valve). This may be used to maintain balance in the centrifuge. When valve A drains it drains into a circular chamber. However if valve B is drained is drains into a holder, preferably a syringe for the PRP. This is located at or close to valve B, thus causing an un-balance in the centrifuge. Valve BC may then be used to drain some light (plasma) component into a balancing container opposite to the PRP container. This permits maintaining the centrifuge balance.

A centrifuge may thus comprise multiple valves that may be actuated to produce one or more separation components of the centrifuge process. The one or more valves may be used to balance the centrifuge. The centrifuge may comprise means to measure the un-balance of the centrifuge. A non-circular part may be thinner than the rest of the chamber. Valves may be located at the thin part of the chamber.

Example 10

Figure 10:
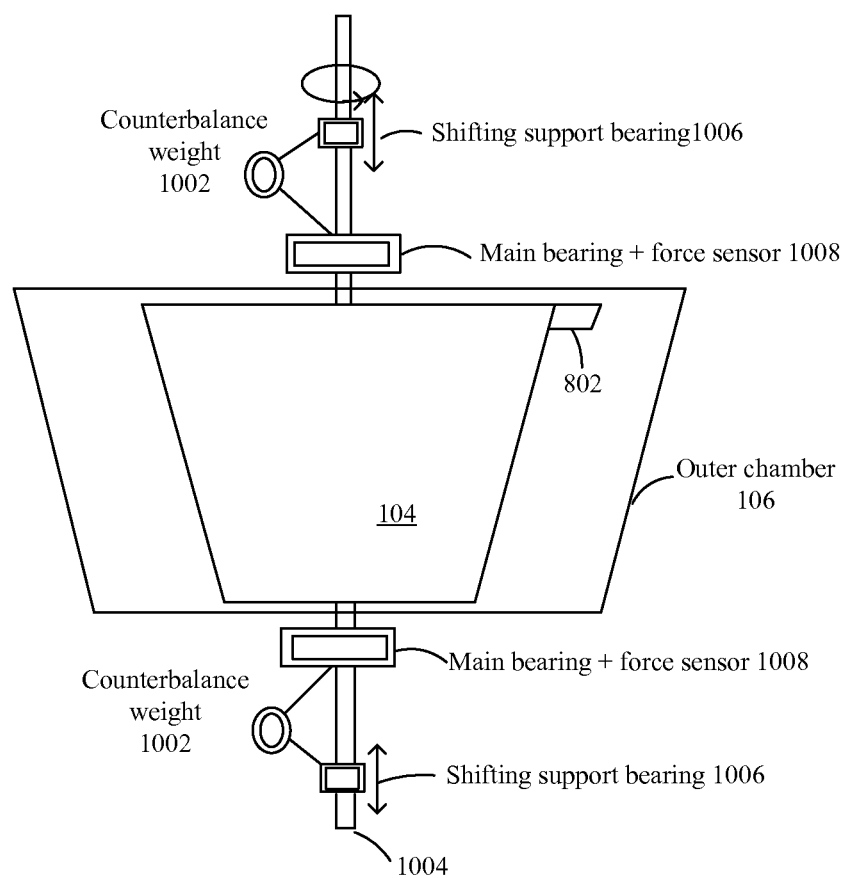

FIG. 10 illustrates a centrifuge with adjustable counter weights 1002. A size and type of a syringe are defined to design the centrifuge and the balancing container. The balancing valve and container may be avoided if the centrifuge has adjustable counter weights 1002 on the axle 1004 (or if the mass permits no counterbalance). These may be realized, for example, by a set of sliding support bearings 1006 with counterbalance weights. The main bearing 1008 is preferably equipped with a force sensor that permits the microcontroller to adjust the counterbalance as needed. This eliminates the needs for precise balancing of the disposable.

In one embodiment a centrifuge has controllable counter weights 1002 to adjust the balance of the centrifuge. The widest part on the upper part of the centrifuge may also reside in the lower part. Furthermore the thinner extension holding the valves may be located in the lowest part of the centrifuge such that even when the centrifuge stops rotating gravity will maintain the desired fluid component separation. Thus in one embodiment the valves are located in the lower part of the centrifuge.

Examples 11-13

Figure 11:
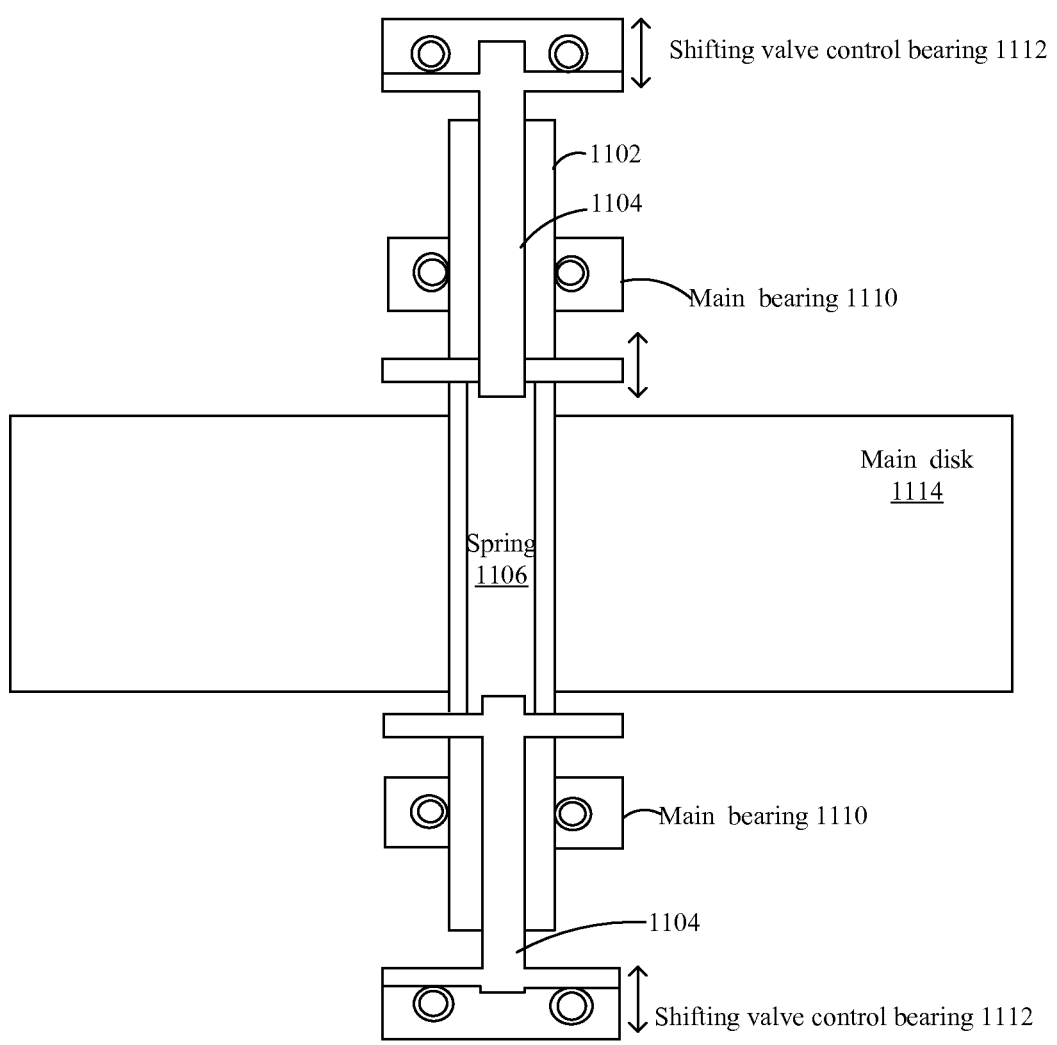
Figure 12:
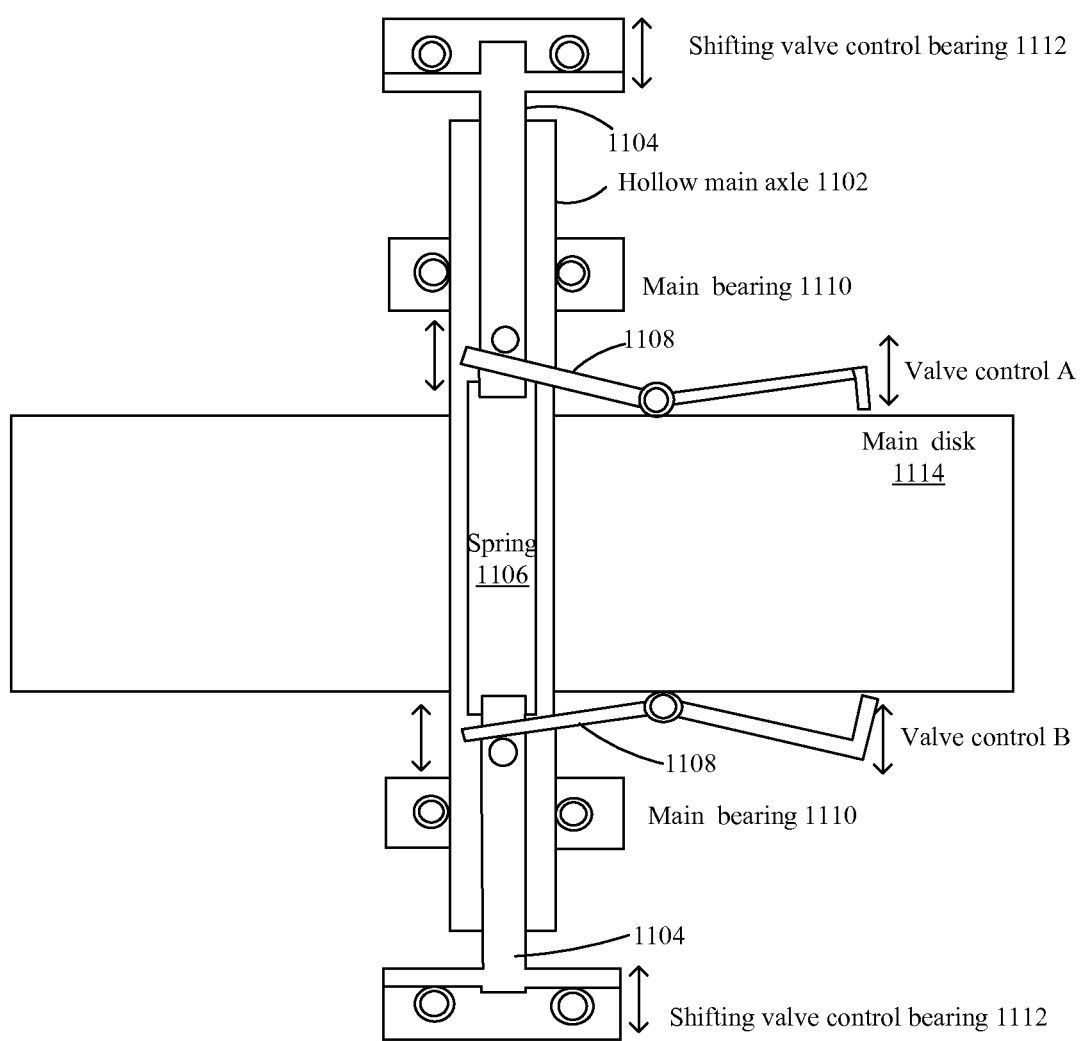
Figure 13:
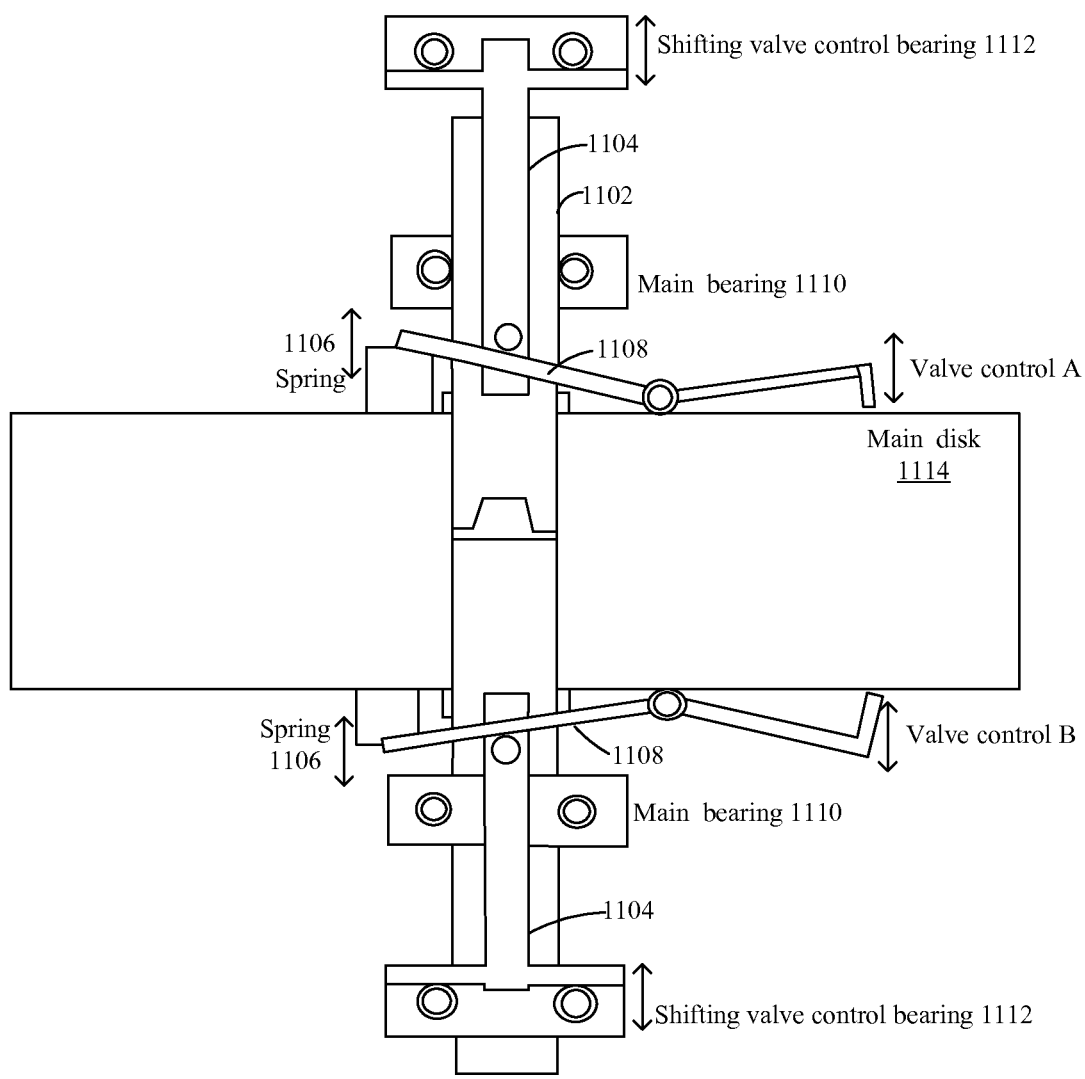

FIGS. 11-13 illustrate a centrifuge with valve control added to a hollow main axis 1102. Inside rods 1104 may be pushed against a spring load 1106. Slits in the main axis 1102 bring out the center rods to push against a lever 1108 controlling the valve. Two valves may be controlled. The counterbalance weight 1002 is used between the main bearing 1110 and the valve control bearings 1112. FIG. 12 shows how the levers 1108 are controlled that push valves on the disposable into a normally closed position. One valve on top and one on bottom is enough for the function.

One problem is that the main disk 1114 cannot be loaded. The main axis 1102 may be split. The springs 1106 become part of the disposable, facilitating a normally closed position of the valves. When the disk 1114 is loaded disk orientation self-centers as grooves in the control levers 1108 line up with the extensions of the push-rods. The top section of the centrifuge axle is then lowered into the bottom section. A lid (with top axle) may be mounted with a hinge (instead of needing to lower it vertically) and that aligns the axle (including rotation).

The levers 1108 should maintain a low profile or be recessed into the main disk 1114 to permit access by the camera 102 and or other observation systems. Thus one centrifuge design includes a disposable that includes valves that rotate with the centrifuge chamber.

Example 14

Figure 14:
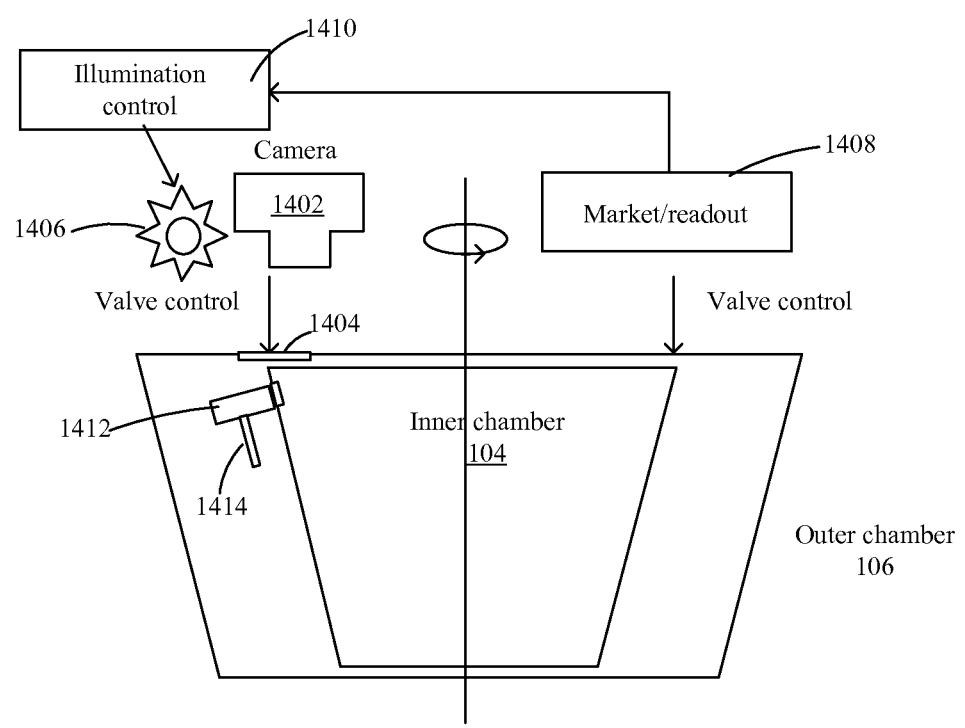

FIG. 14 illustrates a centrifuge in which a color (IR) camera 1402 and/or led/laser systems may be used to observe the demarcation between different blood components. This requires visibility of the interface. The disposable may comprise a hard plastic window 1404 at the location where the valve takes out fluid, where a camera can look through. The valve itself may be a flexible tube that can be squeezed shut, coupled directly behind the window. The disposable is preferably be shaped such that the volume of interest (the amount of expected PRP) fills one camera image to be able to see the (start and) stop of the fraction that is to be selected. The start is implicitly the stop of the red cell separation. As the centrifuge rotates the window 1404 appears at the camera 1403 repeatedly and in between useless image information is presented to the camera 1402. To resolve this either a high speed camera is needed or the camera lighting 1406 is to be modulated 1410. The latter approach involves a pulsing light 1406 source synchronized 1410 with the valve area crossing in front of the camera 1402. Digital averaging of the camera output is typically sufficient to present a picture synchronous with the centrifuge rotation. Synchronization 1410 of valve and light source 1406 is facilitated if the valve has a marker than is observed 1408 optically or electronically. The marker readout 1408 does not need to be co-located with the camera 1402. Proper processing of the marker data permits targeting any location on the disposable that has a known relation to the marker. Another possible solution is to let the camera 1402 spin with the centrifuge, this requires a mechanically stable design of the camera to withstand high G forces but implicitly provides a stable image.

One embodiment of a centrifuge system comprises a non-circular chamber section with integrated optical sensor system where the optical sampling by the sensor is synchronized with the chamber rotation. The system may comprise stroboscopic lighting synchronized with the chamber to synchronize the sampling. The sensor may be a camera. Stroboscopic lighting sequenced with different colors may be used to obtain sensor information at different colors.

Red blood cells may be collected in the outer chamber 106. The valve output for the red blood cells may be a flexible tube that is squeezed by the valve. This tube may drain into the outer chamber 106 that (if reasonably balanced) automatically redistributes it to balance the centrifuge. It could also drain into a non-moving ring that collects the red blood cells, but then the cells will "smash" into the wall of that ring.

One design of a centrifuge system includes at least two main chambers that are approximately balanced; an inner chamber 104 that contains the un-separated start product and at least one intermediate or outer chamber 106 that collects a significant volume of a separation product.

PRP is preferably filled straight into a syringe 1412. The pressure of the centrifuge should be enough to displace the syringe 1412, which may be calculated. When the syringe 1412 is filled (which is aligned tangentially in the main disk such that it can be taken out when the process is done) then at the same time a fraction of the PRP is loaded into a sample holder 1414. The sample holder 1414 may be a tiny syringe or another holder that is connected to a self-sealing valve (open when syringe 1412 is connected, closed otherwise). The sample holder 1414 may be removed to determine platelet count when the PRP has been collected. It typically is not returned to the centrifuge. The main syringe 1412 with PRP may remain in the centrifuge and may get supplemented with plasma in a second spin depending on the platelet count result and the requirements. The final PRP product is produced by the centrifuge after a second spin after that the PRP syringe is taken out of the centrifuge.

Alternately a low-cost platelet counter is integrated in the centrifuge disposable and a tiny fraction of the PRP is sampled by this platelet counter throughout the PRP separation process instead of feeding that fraction to a separate holder. In case the platelet counter needs a dilution fluid this may be blood plasma that is provided from the inner area of centrifuge chamber. To determine the absolute amount of PRP measured by such an integrated platelet counter the small amount of PRP that is sampled may be fed through a pinhole such that droplets are formed that can be observed and counted by a camera. To determine the amount of diluting fluid used in the platelet counter the output of the platelet counter may be collected in a chamber where a volumetric measurement is done.

One design of a centrifuge system includes a syringe spinning with the main chamber that can be filled with the desired fluid component. The centrifuge may comprise a means to tap a sample volume of the component filled into the syringe. The sample component may be filled into a second syringe (typically thinner). The second syringe motion is coupled with the first syringe, and the pressure due to the centrifugal force may be used to press the product into a syringe.

The second spin implies that significant forced is applied to the centrifuge after the test sample is taken out. To prevent contamination of the centrifuge itself, upon removal of the test sample there should be no leakage of any fluid (not even a drop as this will get splattered around when the centrifuge makes the second spin). The centrifuge may be designed to capture leaked fluid after removal of the sample or sample container either by avoiding any leaking or by capturing leaks by gravity and centrifugal force.

The separation may be completely performed on the moving parts of the centrifuge. A complex measurement of platelet count is not available until sample holder (or other device) holding the PRP sample is taken out of the centrifuge. Until that time, the camera information is the primary means available to determine concentration. Information about volume is available by inspecting the main PRP syringe with a camera.

The sample is provided to an analysis station, and the sample container is then discarded. This station may (but need not) be separate from the centrifuge. The collected fluid is injected into the analysis machine, weighed, and diluted for the analysis stage that counts the platelets with a Coulter counter or alternate means. The analysis machine may thus be separate from the handling of the PRP that is used for the patient and thus does not need to be sterile. Thus in one design the centrifuge system composition measurement system is not sterile and provided with a sample in a sample container taken out of the sterile centrifuge section of the system.

After platelet count is determined and target values have been determined using the software database, an instruction can be provided for the amount of plasma to be added to arrive at the proper concentration. This process may be automated in the centrifuge by controlling the volume of plasma to be added.

Examples 15 & 16

Figure 15:
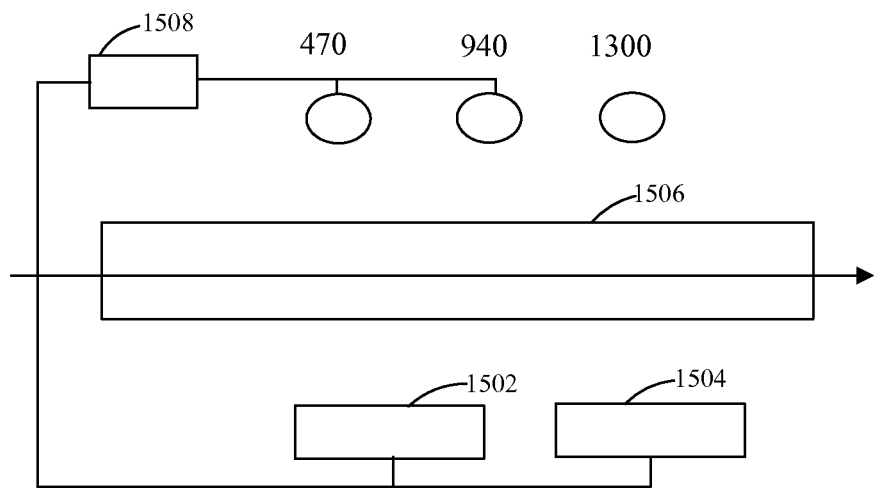
Figure 16:
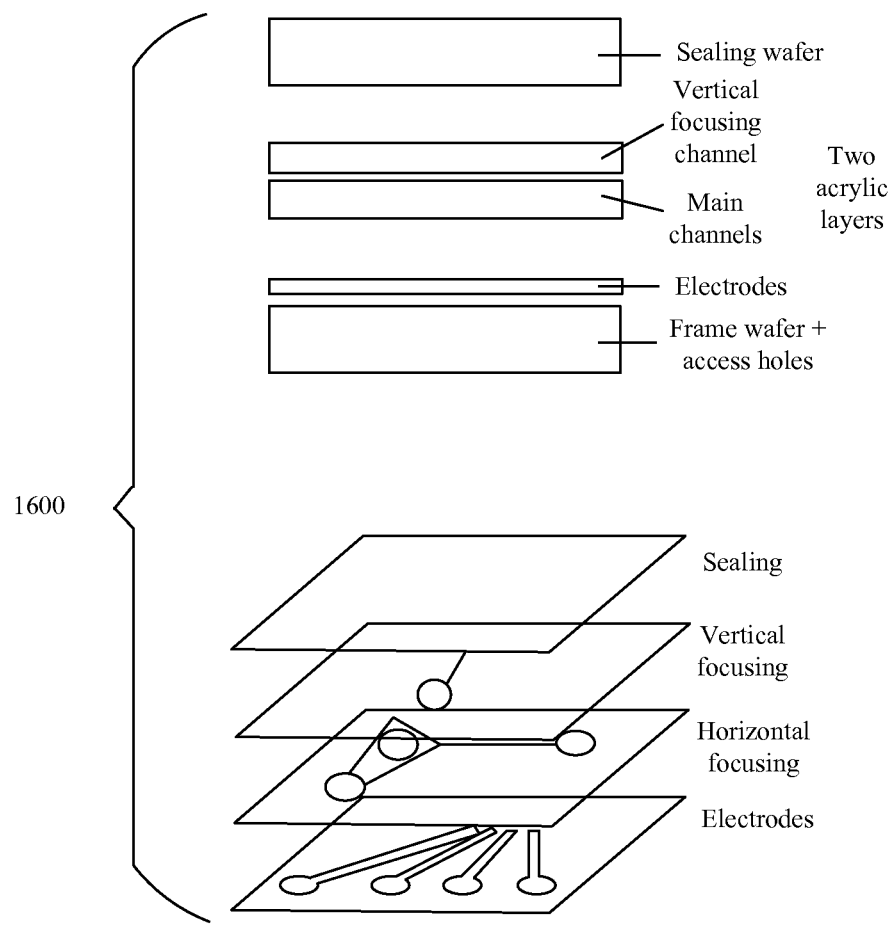

FIGS. 15 and 16 show possible designs of a sensor 1600 and sensor system for a centrifuge. Platelet concentration of whole blood and PRP may be measured. Sensor design options include but are not limited to optical, MIE scattering, IMC, impedance, electrical, and eddy current. One design of a sensor 1600 is a hydrodynamic focusing platform based on solid adhesives.

In one embodiment the sensing system comprises three LEDs (light emitting diodes) and two photodiode light detectors. The three LEDs have wavelengths of 470 nm, 940 nm, and 1300 nm. The light generated by the 470 nm and the 940 nm LEDs is detected by one of the detectors/photodiodes 1502, while light generated by the 1300 nm LED is detected by the other photodiode 1504. Because the detector/photodiode 1502 sensing the 470 nm and 940 nm light is also sensitive to room light, Time Division Multiplexing is utilized with the LED signals, with a time window dedicated to all LEDs off. In this method, the light emitted from each LED is electronically chopped by pulsing the LEDs on and off in sequence. The detector/photodiode response is then sampled so that any signal due to the ambient background light can be canceled out.

Blood flows through a transparent chamber 1506 (preferably comprising polycarbonate) having a near-elliptical cross section. LEDs are positioned so that light travels perpendicular to the path of the blood flow. The sides of the chamber 1506 through which light passes preferably are flat. The second detector/photodiode 1504 is more responsive to the 940 nm light. Accordingly, the 470 nm LED is set so that it shines directly at the detector 1502, while the 940 nm LED is positioned off-center.

Because absorption and scattering characteristics are functions of wavelength, it is preferred to use different wavelengths originating from different LEDs. The use of different wavelengths enables the detection of various blood components. A 470 nm LED provides light having both high intensity and short wavelength. This wavelength will be scattered by both platelets and red blood cells. A wavelength of 470 nm is also strongly absorbed by red blood cells. A wavelength of 940 nm is neither scattered nor absorbed as strongly as a wavelength of 470 nm. The 1300 nm wavelength is not absorbed by the red blood cells and scattering is not as significant as with the shorter wavelengths.

Although both the absorption and the scatter drop off as the wavelength increases, the change is not the same for the two effects. Therefore, the use of three different wavelengths yields a great deal of relevant information.

The intensity of the light emitted from the LEDs is electronically adjustable through a current sensing, voltage feedback amplifier 1508. The signal from the detector 1508 is monitored, while the intensity of the light is adjusted, until the signal falls within a pre-defined window. This process is accomplished automatically in software for each new sample. This calibration process does not require an operator.

The intensity of each LED is adjusted and set by software running, for example, on a single board computer with a 16 bit data bus. The lower 8 bits are used to adjust the intensity through a Digital to Analog converter. The analog voltage produced at the converter is used to adjust the current through the LED.

The voltage of the "Sensor 470 Intensity" signal ranges from 0 to 5 volts. When the "Sensor 470 Enable" signal is greater than 2.5 volts, the intensity voltage is applied to the non-inverting input of the Op Amp. (When the enable signal is less than 2.5 volts, the non-inverting input of the Op Amp is shorted to ground through the open collector comparator. The enable signal is digital, and is therefore either 0 or 5 volts.) The feedback on the Op Amp is used to apply the same voltage as the intensity signal across the load resistor.

Therefore, the current through the LED is equal to the voltage of "Sensor 470 Intensity" divided by the value of the load resistor.

The load resistor is sized to limit the current through the LED to a value that will not cause it damage. The transistor is used in the output circuit of the Op Amp to prevent the Op Amp from having to source all the current for the LED.

When a new disposable set is used, the software adjusts the intensity of the LEDs until the signal at the detector is within a pre-defined window. In this way, the apparatus of this invention compensates for variation in disposables, variation in disposable location, and any aging effect on the LEDs or detector elements. If this automatic calibration fails to adjust the LED intensities to the required value, the machine will not allow operation.

Once the intensity of all three LEDs is set, with the disposable in place, the apparatus can be used to separate the sample of the patient's blood into the desired components. The transmittance of light through the blood is monitored in the disposable whenever the pump is running. The software makes decisions based on the transmittance values, ratios of transmittance values, and the derivatives of these values with respect to time.

The blood components are identified by the intensity of the light transmitted through the blood and by the derivative of the intensity as a function of time. Because the blood is flowing through the sensor while the light intensity is being sampled, the derivative of the intensity is also a function of blood volume passing through the sensor. The components that are identified are (1) whole blood; (2) clean plasma (low platelet count, and low Hct); (3) platelet rich plasma; (4) high Hct plasma; and (5) air.

Figure 17:
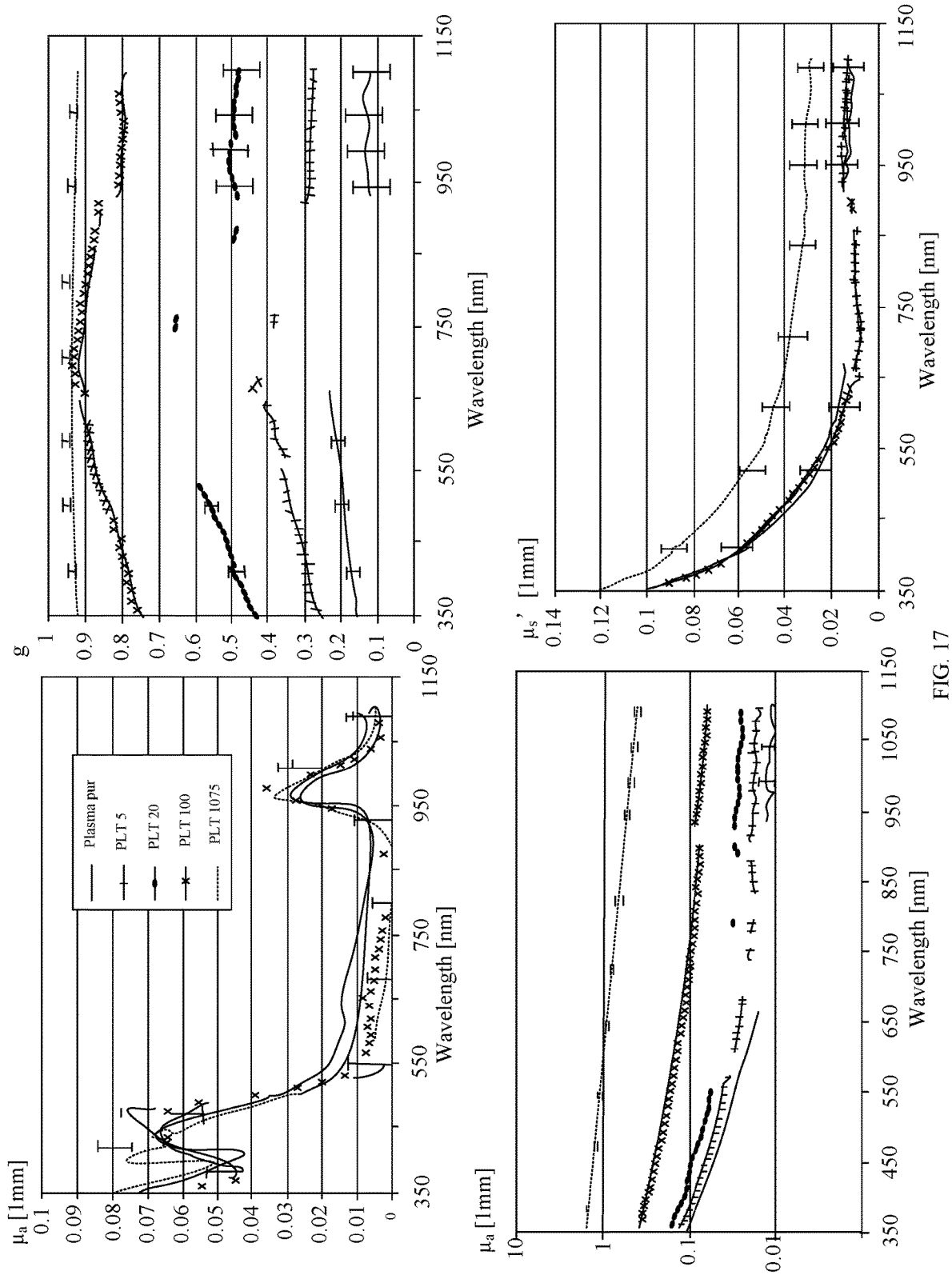
Figure 18:
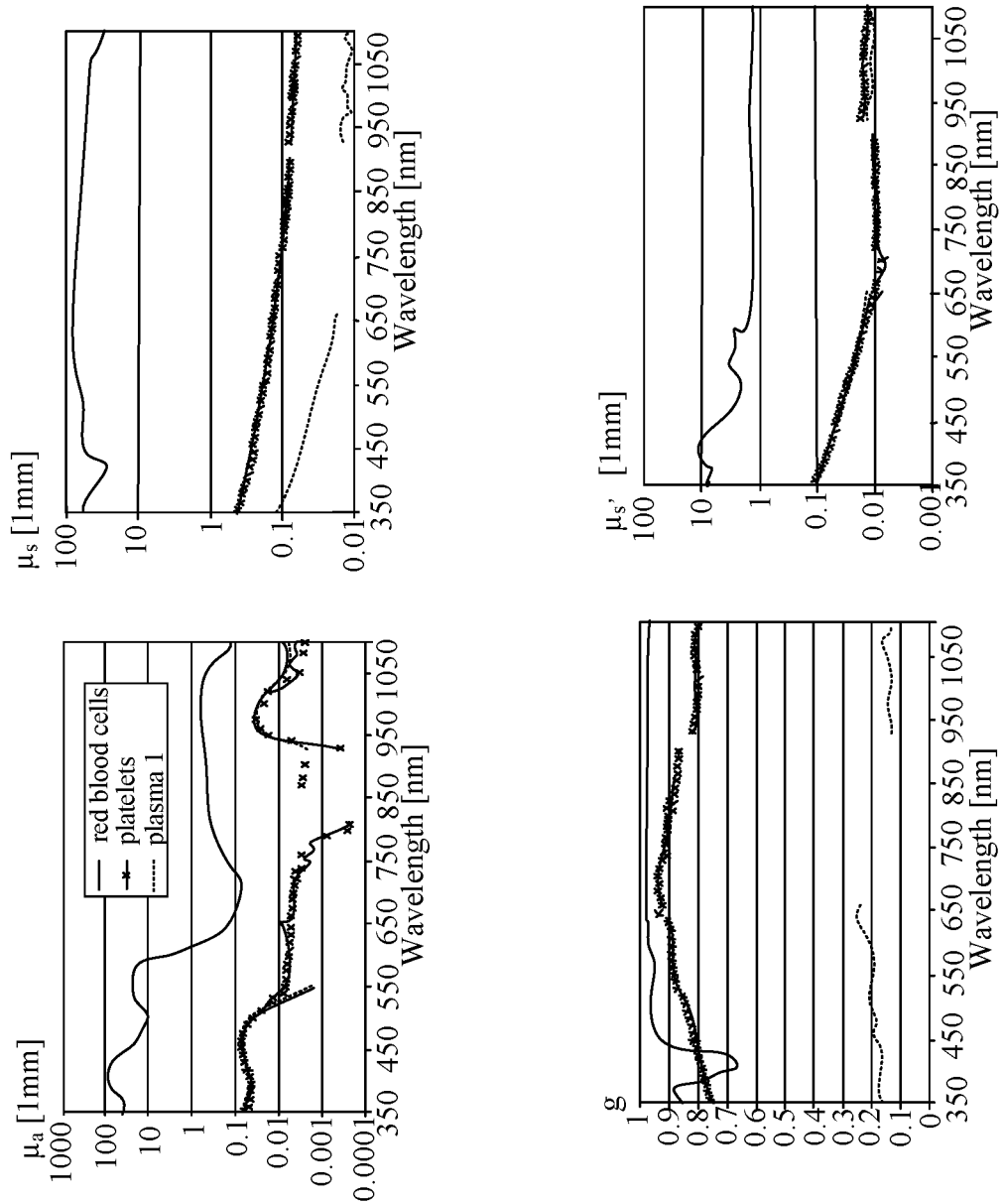

FIG. 17 and FIG. 18

These figures show the response of the above-described sensor implementation to various fluid materials.

Implementations and Alternatives

The techniques and procedures described herein may be implemented via logic distributed in a centrifuge and/or one or more associated devices. The particular distribution and choice of logic is a design decision that will vary according to implementation.

Those having skill in the art will appreciate that there are various logic implementations by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

What is claimed is:

1. A disposable component for use in a centrifuge, the disposable component comprising:
   a non-circular first chamber to hold a fluid sample while the disposable component is spinning in the centrifuge;
   a second chamber coupled to the first chamber by one or more valves;
   the valves configured to rotate with the first chamber and to migrate a separated component of the fluid sample to the second chamber while the disposable component is spinning in the centrifuge;
   an optical sensor system configured to determine, while the disposable component is spinning in the centrifuge, a composition of one or both of (a) the separated component of the fluid sample in the second chamber, and (b) a remainder component of the fluid sample spinning in the first chamber;
   wherein the first chamber is elliptical; and
   the one or more valves comprising a first valve at one end of a long axis of the elliptical first chamber and a second valve at the other end of the long axis of the elliptical first chamber.

2. The disposable component of claim 1, wherein the elliptical first chamber is egg-shaped.

3. The disposable component of claim 2, the one or more valves comprising:
   a first valve located at a first radial distance from an axis of rotation of the elliptical first chamber;
   a second valve located at a second radial distance from the axis of rotation of the elliptical first chamber; and
   wherein the first distance is less than the second distance.

4. The disposable component of claim 1, wherein the elliptical first chamber is off-center from an axis of rotation of the elliptical first chamber.

5. A disposable component for use in a centrifuge, the disposable component comprising:
   a first chamber and a second chamber;
   the first chamber shaped to be asymmetrical across at least one axis in a plane of rotation;
   the first chamber comprising at least one valve to permit material flow from the first chamber to the second chamber;
   the at least one valve positioned within the first chamber such that, due to the asymmetrical shape of the first chamber, heavier components of a fluid sample spinning within the first chamber migrate to the valve preferentially over lighter components of the fluid sample;
   an optical sensor system configured to determine, while the disposable component is spinning in the centrifuge, a composition of separated components of the fluid sample within the first chamber, the second chamber, or both; and
   wherein stroboscopic lighting sequenced with different colors is applied to synchronize optical sampling by an integrated sensor system with the rotation of the centrifuge chamber to obtain sensor information at different colors.

6. The disposable component of claim 5, configured such that controlled opening and closing the valve may be performed while the disposable component is spinning.

7. The disposable component of claim 5, wherein the first chamber and the second chamber comprise, respectively, an inner chamber that retains the fluid sample and an outer chamber that collects the separated components, the inner chamber and the outer chamber configured to spin coaxially, and the at least one valve positioned on a circumferential wall of the inner chamber.

8. The disposable component of claim 5, wherein the optical sensor system comprises a camera.

9. The disposable component of claim 5, wherein the optical sensor system is configured to determine the hematocrit value of one or more of the separated components.

10. The disposable component of claim 5, wherein the first chamber is elliptical or egg shaped.

* * * * *